United States Patent [19]

Mittendorf et al.

[11] Patent Number: 5,321,042
[45] Date of Patent: Jun. 14, 1994

[54] USE OF SUBSTITUTED TETRAHYDROTHIOPHENES, SOME OF WHICH ARE KNOWN, AS MEDICAMENTS, NEW ACTIVE SUBSTANCES AND PROCESSES FOR THEIR PREPARATION

[75] Inventors: Joachim Mittendorf, Wuppertal; Franz Kunisch, Odenthal-Gloebusch; Manfred Plempel, Haan, all of Fed. Rep. of Germany

[73] Assignee: Bayer Aktiengesellschaft, Leverkusen, Fed. Rep. of Germany

[21] Appl. No.: 958,852

[22] Filed: Oct. 8, 1992

[30] Foreign Application Priority Data

Oct. 22, 1991 [DE] Fed. Rep. of Germany ....... 4134755

[51] Int. Cl.$^5$ .............................................. A61K 31/38
[52] U.S. Cl. .................................................... 514/447
[58] Field of Search ........................... 514/447; 549/68

[56] References Cited

U.S. PATENT DOCUMENTS

| | | | |
|---|---|---|---|
| 2,453,564 | 11/1948 | Baker | 549/68 |
| 3,655,692 | 4/1972 | Shen et al. | 549/68 |
| 4,520,028 | 5/1985 | Adams et al. | 514/447 |
| 4,847,386 | 7/1989 | Barker et el. | 549/68 |

FOREIGN PATENT DOCUMENTS 0116932 8/1984 European Pat. Off. .
0331919 9/1989 European Pat. Off. .
0365089 4/1990 European Pat. Off. .

OTHER PUBLICATIONS

Journal of Organic Chemistry, vol. 12, 1947, pp. 174–185.
E. L. Eliel, Stereochemistry of Carbon Compounds, McGraw Hill, 1962.
J. C. Sheehan et al., J. Am. Chem. Soc. 95, 875 (1973).
F. E. Frerman et al., J. Biol. Chem. 225, No. 5, pp. 2199–2202 (1980).
N. B. Bengton et al., Int. Pept. Prot. Res. 13, 403 (1979).
G. M. Benora, et al., Int. Pept. Prot. Res. 17, 403 (1981).
Houben–Weyl, "Methoden der organischen Chemie", vol. XI/1 and XI/2; (1957).
Houben–Weyl, "Methoden der organischen Chemie", vol. IX, pp. 407 ff; (1958) Beilstein 11, p. 26.
Fieser 1, 1236; 3, 316; 5, 719; 6, 632; 7, 394; 9, 21; 10, 14; (1970).
Bull. Chem. Soc. Jpn. 40(11), 2636–2640 (1967).
Chem. Ber. 123 (1990), pp. 1999–2014.

Primary Examiner—Frederick E. Waddell
Assistant Examiner—Raymond J. Henley, III
Attorney, Agent, or Firm—Sprung Horn Kramer & Woods

[57] ABSTRACT

The invention relates to the use of substituted tetrahydrothiophenes, some of which are known, as medicaments, in particular as antimycotic agents, to new active substances and to processes for their preparation.

5 Claims, No Drawings

USE OF SUBSTITUTED TETRAHYDROTHIOPHENES, SOME OF WHICH ARE KNOWN, AS MEDICAMENTS, NEW ACTIVE SUBSTANCES AND PROCESSES FOR THEIR PREPARATION

The invention relates to the use of substituted tetrahydrothiophenes, some of which are known, as medicaments, in particular as antimycotic agents, to new active substances and to processes for their preparation.

It has already been disclosed that 2,5-diaryl-tetrahydrothiophenes are antagonists of platelet-activating factor [cf. EP 365,089 A]. In addition, in the publication J. Org. Chem. 12, (1947) 174, 180 the compound ($\pm$)-trans-4-ethoxycarbonylamino-tetrahydrothiophene-3-carboxylic acid is described without pharmacological action.

It has now been found that the substituted tetrahydrothiophenes of the general formula (I)

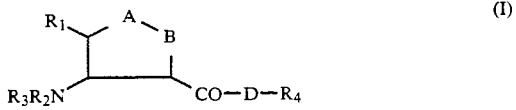

in which

A and B are always different and represent a sulphur atom or the group of the formula —SO,—SO$_2$ or —CHR$^5$,
in which R$^5$ denotes hydrogen or straight-chain or branched alkyl having up to 8 carbon atoms, which is optionally substituted by halogen, hydroxyl, phenyl or carboxyl or by straight-chain or branched alkoxy or alkoxycarbonyl each having up to 6 carbon atoms, R$^1$ represents hydrogen or straight-chain or branched alkyl having up to 8 carbon atoms, which is optionally substituted 1 or 2 times by identical or different substituents from the series comprising halogen, hydroxyl, phenyl and carboxyl or by straight-chain or branched alkoxy, acyl or alkoxycarbonyl each having up to 6 carbon atoms or by a group of the formula —NR$^6$R$^7$,
in which R$^6$ and R$^7$ are identical or different and denote hydrogen, phenyl or straight-chain or branched alkyl having up to 6 carbon atoms, R$^2$ represents hydrogen or represents straight-chain or branched alkyl having up to 8 carbon atoms, which is optionally substituted 1 or 2 times by identical or different substituents from the series comprising hydroxyl and formyl or by straight-chain or branched acyl having up to 6 carbon atoms or by phenyl or benzoyl, each of which is optionally substituted up to 2 times by identical or different substituents from the series comprising halogen, nitro and cyano, or by straight-chain or branched alkyl having up to 6 carbon atoms,
or
represents straight-chain or branched acyl having up to 8 carbon atoms,
or
represents benzoyl which is optionally substituted as described above,
or
represents a group of the formula —SO$_2$R$^8$,
in which R$^8$ denotes straight-chain or branched alkyl having up to 8 carbon atoms, or benzyl or phenyl, where the latter are optionally substituted up to 3 times by identical or different substituents from the series comprising halogen, hydroxyl, nitro, cyano, trifluoromethyl and trifluoromethoxy or by straight-chain or branched alkyl, alkoxy or alkoxycarbonyl each having up to 6 carbon atoms, carboxyl or by the abovementioned group —NR$^6$R$^7$,
in which R$^6$ and R$^7$ have the abovementioned meaning, represents phenyl which is optionally substituted up to 3 times by identical or different substituents from the series comprising halogen, hydroxyl, nitro, trifluoromethyl, trifluoromethoxy, straight-chain or branched alkyl, acyl, and alkoxy or alkoxycarbonyl each having up to 6 carbon atoms or by a group of the formula —NR$^6$R$^7$ or —SO$_2$R$^8$,
in which R$^6$, R$^7$ and R$^8$ have the abovementioned meaning, R$^3$ represents hydrogen or straight-chain or branched alkyl having up to 8 carbon atoms, which is optionally substituted by phenyl,
or R$^2$ and R$^3$ together represent the radical of the formula =CHR$^{5'}$,
in which R$^{5'}$ has the abovementioned meaning of R$^5$ and is identical to or different from this, D represents an oxygen or sulphur atom or the

group,

R$^4$ represents hydrogen or straight-chain or branched alkyl having up to 8 carbon atoms, or phenyl, where the latter are optionally substituted up to 3 times by identical or different substituents from the group comprising hydroxyl, halogen, nitro, cyano, carboxyl, trifluoromethyl and trifluoromethoxy, by straight-chain or branched alkoxy, in the case of phenyl also by alkyl, acyl or alkoxycarbonyl each having up to 6 carbon atoms or by a group of the formula —NR$^6$R$^7$ or —SO$_2$R$^8$,
in which R$^6$, R$^7$ and R$^8$ have the abovementioned meaning,
or for the case in which D represents the

group

R$^4$ represents the group of the formula —SO$_2$R$^8$,
in which

R$^8$ has the abovementioned meaning,
surprisingly exhibits a potent antimicrobial action, in particular potent antimycotic action, against dermatophytes, budding fungi and biphasic fungi and are thus suitable for use in the control of dermatomycoses and systemic mycoses.

The physiologically acceptable acid addition salts and metal salt complexes of the compounds of the general formula (I) and the racemic modifications, the antipodes, the diastereomeric mixtures and the individual isomers are also preferred for this use.

Preferably used compounds of the general formula (I) are those
in which

A and B are always different and represent a sulphur atom or the group of the formula —SO, —SO$_2$ or —CHR$^5$,
in which R$^5$ denotes hydrogen or straight-chain or branched alkyl having up to 6 carbon atoms, which is optionally substituted by halogen or hydroxyl, or by straight-chain or branched alkoxy or alkoxy carbonyl each having up to 4 carbon atoms, R$^1$ represents hydrogen or straight-chain or branched alkyl having up to 6 carbon atoms, which is optionally substituted by halogen or hydroxyl, by straight-chain or branched alkoxy, acyl or alkoxy carbonyl each having up to 4 carbon atoms or by a group of the formula —NR$^6$R$^7$,
in which R$^6$ and R$^7$ are identical or different and denote hydrogen or straight-chain or branched alkyl having up to 4 carbon atoms, R$^2$ represents hydrogen or represents straight-chain or branched alkyl having up to 6 carbon atoms, which is optionally substituted by hydroxyl or formyl or by straight-chain or branched acyl having up to 4 carbon atoms or by phenyl or benzoyl, each of which is optionally substituted by halogen, nitro or cyano, or by straight-chain or branched alkyl having up to 4 carbon atoms, or represents straight-chain or branched acyl having up to 6 carbon atoms or represents benzoyl which is optionally substituted as described above, or represents a group of the formula —SO$_2$R$^8$,
in which R$^8$ denotes straight-chain or branched alkyl having up to 6 carbon atoms, phenyl or benzyl, where the latter are optionally substituted up to 2 times by identical or different substituents from the series comprising halogen, hydroxyl, nitro, cyano, trifluoromethyl and trifluoromethoxy or by straight-chain or branched alkyl or alkoxy each having up to 4 carbon atoms or by the abovementioned group of the formula —NR$^6$R$^7$,
in which R$^6$ and R$^7$ have the abovementioned meaning, represents phenyl which is optionally substituted up to 2 times by identical or different groups from the series comprising halogen, hydroxyl, nitro, trifluoromethyl, trifluoromethoxy and straight-chain or branched alkyl, acyl, alkoxy or alkoxycarbonyl each having up to 4 carbon atoms or by a group of the formula —NR$^6$R$^7$ or —SO$_2$R$^8$,
in which R$^6$, R$^7$ and R$^8$ have the abovementioned meaning, R$^3$ represents hydrogen or straight-chain or branched alkyl having up to 6 carbon atoms or benzyl,
or R$^2$ and R$^3$ together represent the radical of the formula =CHR$^5'$,
in which R$^5'$ has the abovementioned meaning of R$^5$ and is identical to or different from this.

D represents an oxygen or sulphur atom or the

group,

R$^4$ represents hydrogen or straight-chain or branched alkyl having up to 6 carbon atoms or phenyl, where the latter are optionally substituted up to 2 times by identical or different substituents from the series comprising hydroxyl, halogen, nitro, cyano, trifluoromethyl and trifluoromethoxy, by straight-chain or branched alkoxy, acyl or alkoxy carbonyl each having up to 4 carbon atoms or by a group of the formula —NR$^6$R$^7$ or —SO$_2$R$^6$,
in which R$^6$, R$^7$ and R$^8$ have the abovementioned meaning, or for the case in which D represents the

group,

R$^4$ represents the group of the formula —SO$_2$R$^8$,
in which

R$^8$ has the abovementioned meaning,
if appropriate in an isomeric form and their physiologically acceptable acid addition salts and metal salt complexes in the control of dermatomycoses and systemic mycoses.

Particularly preferably used compounds of the general formula (I) are those
in which A and B are always different and represent a sulphur atom or the group of the formula —SO, —SO$_2$ or —CHR$^5$,
in which R$^5$ denotes hyrogen or straight-chain or branched alkyl having up to 4 carbon atoms, R$^1$ represents hydrogen or represents straight-chain or branched alkyl having up to 4 carbon atoms, R$^2$ represents hydrogen or represents straight-chain or branched alkyl having up to 4 carbon atoms, or represents straight-chain or branched acyl having up to 4 carbon atoms, or represents a group of the formula —SO$_2$R$^8$,
in which R$^8$ denotes straight-chain or branched alkyl having up to 4 carbon atoms, phenyl or benzyl, where the latter are optionally substituted by hydroxyl, fluorine, chlorine, bromine, nitro, cyano, methyl, ethyl or methoxy, R$^3$ represents hydrogen or represents straight-chain or branched alkyl having up to 4 carbon atoms,
or R$^2$ and R$^3$ together represent the radical of the formula =CHR$^5'$,
in which R$^5'$ has the abovementioned meaning of R$^5$ and is identical to or different from this, D represents an oxygen or a sulphur atom or the

group,

R$^4$ represents hydrogen or straight-chain or branched alkyl having up to 4 carbon atoms or phenyl, where the latter are optionally substituted by fluorine, chlorine, bromine, nitro, cyano, methoxy or ethoxy or by a group of the formula —NR$^6$R$^7$ or —SO$_2$R$^8$,
in which R$^6$ and R$^7$ are identical or different and denote hydrogen, methyl or ethyl
and R$^8$ has the abovementioned meaning, or in the case in which D represents the

group,

R$^4$ represents the group of the formula —SO$_2$R$^8$,
in which

R$^8$ has the abovementioned meaning,
if appropriate in an isomeric form, and their physiologically acceptable acid addition salts and metal salt complexes in the control of dermatomycoses and systemic mycoses.

Very particularly preferably used compounds of the general formula (I) are those in which both substituents —NR$^2$R$^3$ and —CO—D—R$^4$ are present in the cis-position in the control of dermatomycoses and systemic mycoses.

The invention additionally relates to new compounds of the general formula (Ia)

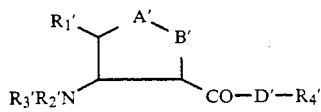

in which

A' and B' are always different and represent a sulphur atom or the group of the formula —SO, —SO$_2$ or —CHR$^9$,
in which R$^9$ denotes hydrogen or straight-chain or branched alkyl having up to 8 carbon atoms, which is optionally substituted by halogen, hydroxyl, phenyl or carboxyl or by straight-chain or branched alkoxy carbonyl each having up to 6 carbon atoms, R$^{1'}$ represents hydrogen or straight-chain or branched alkyl having up to 8 carbon atoms, which is optionally substituted 1 or 2 times by identical or different substituents from the series comprising hologen, hydroxyl, phenyl or carboxyl or by straight-chain or branched alkoxy, acyl or alkoxy carbonyl each having up to 6 carbon atoms or by a group of the formula —NR$^{6'}$R$^{7'}$,
in which R$^{6'}$ and R$^{7'}$ are identical or different and denote hydrogen, phenyl or straight-chain or branched alkyl having up to 6 carbon atoms, R$^{2'}$ represents or represents straight-chain or branched alkyl having up to 8 carbon atoms, which is optionally substituted 1 or 2 times by identical or different groups from the series comprising hydroxyl and formyl or by straight-chain or branched acyl having up to 6 carbon atoms or by phenyl or benzoyl, each of which is optionally substituted up to 2 times by identical or different substituents from the series comprising halogen, nitro and cyano, or by straight-chain or branched alkyl having up to 6 carbon atoms, or represents straight-chain or branched acyl having up to 8 carbon atoms, or represents benzoyl which is optionally substituted as described above, or represents a group of the formula —SO$_2$R$^{8'}$,
in which R$^{8'}$ denotes straight-chain or brached alkyl having up to 8 carbon atoms, benzyl or phenyl, where the latter are optionally substituted up to 3 times byt identical or different substituents from the series comprising halogen, hydroxyl, nitro, cyano, trifluoromethyl and trifluoromethoxy or by straight-chain or branched alkyl, alkoxy or alkoxycarbonyl each having up to 6 carbon atoms, carboxyl or by the abovementioned group —NR$^{6'}$R$^{7'}$,
in which R$^{6'}$ and R$^{7'}$ has the abovementioned meaning,
represents phenyl which is optionally substituted up to 3 times by identical or different substituents from the series comprising halogen, hydroxyl, nitro, trifluoromethyl, trifluoromethoxyand straight-chain or branched alkyl, acyl, alkoxy or alkoxycarbonyl each having up to 6 carbon atoms or by a group of the formula —NR$^{6'}$R$^{7'}$ or —SO$_2$R$^{8'}$,
in which R$^{6'}$, R$^{7'}$ and R$^{8'}$ have the abovementioned meaning, R$^{3'}$ represents hydrogen or straight-chain or branched alkyl having up to 8 carbon atoms, which is optionally substituted by phenyl,
or R$^{2'}$ and R$^{3'}$ together represent the radical of the formula =CHR$^{9'}$,
in which R$^{9'}$ has the abovementioned meaning of R$^9$ and is identical to or different from this, D' represents an oxygen or sulphur atom or the

group,

R$^{4'}$ represents hydrogen or straight-chain or branched alkyl having up to 8 carbon atoms or phenyl, where the latter are optionally substituted up to 3 times by identical or different substituents from the series comprising hydroxyl, halogen, nitro, cyano, carboxyl, trifluoromethyl and trifluoromethoxy, by straight-chain or branched alkoxy, in the case of phenyl also by alkyl, acyl or alkoxycarbonyl each having up to 6 carbon atoms or by a group of the formula —NR$^{6'}$R$^{7'}$ or —SO$_2$R$^{8'}$,
in which R$^{6'}$, R$^{7'}$ and R$^{8'}$ have the abovementioned meaning or for the case in which D represents the

group,

R$^{4'}$ represents the group of the formula —SO$_2$R$^{8'}$, in which

R$^{8'}$ has the abovementioned meaning, with the proviso that if A' represents a sulphur atom, B' represents the —CH$_2$— group, D' represents an oxygen atom and R$^{1'}$, R$^{2'}$, R$^{3'}$ and R$^{4'}$ represent hydrogen, the two substituents —NR$^{2'}$R$^{3'}$ and —CO—D'—R$^{4'}$ must not both be present in the trans-position.

The compounds of the general formulae (I) and (Ia) according to the invention can also be present in the form of their salts. In general, salts with organic or inorganic bases or acids may be mentioned here.

The acids which can be added preferably include hydrohalic acids, such as, for example, hydrochloric acid and hydrobromic acid, in particular hydrochloric acid, and also phosphoric acid, nitric acid, sulphuric acid, mono-and bifunctional carboxylic acids and hydroxy carboxylic acids, such as, for example, acetic acid, maleic acid, malonic acid, oxalic acid, gluconic acid, succinic acid, fumaric acid, tartaric acid, citric acid, salicylic acid, sorbic acid and lactic acid as well as sulphonic acids, such as, for example, p-toluenesulphonic acid, 1,5-naphthalenedisulphonic acid or camphorsulphonic acid.

Physiologically acceptable salts can also be metal or ammonium salts of the compounds according to the invention which have a free carboxyl group. Those particularly preferred are, for example, sodium, potassium, magnesium or calcium salts, and anunoniumsalts which are derived from ammonia, or organic amines such as, for example, ethylamine, di- or triethylamine, di- or triethanolamine, dicyclohexylamine, dimethylaminoethanol, arginine, lysine or ethylenediamine.

The compounds of the general formulae (I) and (Ia) according to the invention can exist in stereoisomeric forms, for example either as image and mirror image (enantiomers), or which do not behave as image and mirror image (diasteromers), or are present as a diasteromer mixture or as pure cis- or trans-isomers. The invention relates both to the antipodes, racemic modifications and diasteromer mixtures and to the pure isomers. The racemic modifications, like the diasteromers, can also be separated in a known manner into the stereoisomerically uniform constituents [cf. E. L. Eliel, Stereochemistry of Carbon Compounds, McGraw Hill, 1962]. Separation into the stereoisomerically uniform compounds is carried out, for example, by means of a chromatographic resolution of diastereomeric esters and amides or on optically active phases. In addition, crystallisation of diastereomeric salts is possible.

The compounds of the general formula (I) according to the invention and the new compounds of the general formula (Ia) and their acid addition salts and metal salt complexes have antimicrobial actions, in particular potent antimycotic actions. They have a very broad spectrum of antimycotic action, in particular against dermatophytes and budding fungi as well as hipbasic fungi, for example against Candida species such as *Candida albicans*, Epidermophyton species such as *Epidermophyton floccosum*, Aspergillus species such as *Aspergillus niger* and *Aspergillus fumigatus*, Trichophyton species such as *Trichophyton mentagrophytes*, Microsporon species such as *Microsporon felineum* and Torulopsis species, such as *Torulopsis glabrata*. The enumeration of these microorganisms in no way represents a restriction of the microorganisms which can be controlled, but is of only illustrative character.

Indication examples which may be mentioned in human medicine are, for example: Dermatomycoses and systemic mycoses caused by *Trichophyton mentagrophytes* and other Trichophyton species, Microsporon species and *Epidermophyton floccosum*, budding fungi and biphasic fungi as well as mould fungi.

Indication areas in veterinary medicine which may be mentioned are, for example: All dermatomycoses and systemic mycoses, in particular those which are caused by the abovementioned pathogens.

The compounds of the general formulae (I) and (Ia) can be prepared by a process in which

[A]in the case in which A and A' each correspondingly represent the —CHR$^5$ or —CHR$^9$ group and B or B' represents a sulphur atom, compounds of the general formula (II)

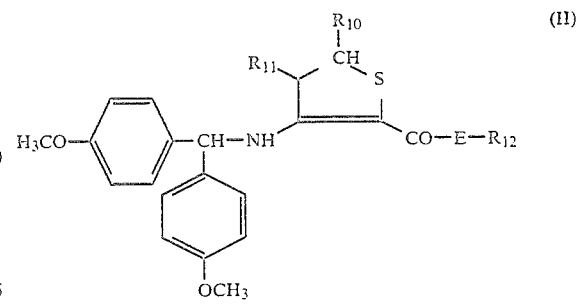

in which

R$^{10}$ encompasses the abovementioned meaning of R$^5$ and R$^9$,

R$^{11}$ encompasses the abovementioned scope of meaning of R$^1$ and R$^{1'}$,

E represents an oxygen atom and

R$^{12}$ represents C$_1$-C$_6$-alkyl, are first converted with sodiumcyanoborohydride in inert solvents into the compounds of the general formula (III)

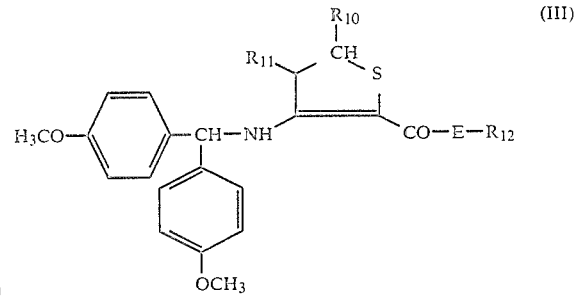

in which

R$^{10}$, R$^{11}$, R$^{12}$ and E have the abovementioned meaning, and the amine function is then deblocked with acids and water, preferably acetic acid, or

[B] in the case in which A and A' represent a sulphur atom and B or B' represents the —CHR$^5$ or —CHR$^9$ group,
compounds of the general formula (IV)

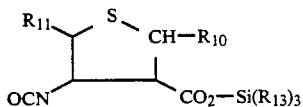
(IV)

in which
R$^{10}$ and R$^{11}$ have the abovementioned meaning
and
R$^{13}$ represents a C$_1$-C$_3$-alkyl radical,
are reacted in ethers, preferably diethyl ether, in the presence of water
first to give the compounds of the general formula (V)

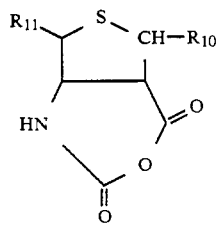
(V)

in which
R$^{10}$ and R$^{11}$ have the abovementioned meaning,
and in a next step converted with acids, preferably hydrochloric acid, and subsequently propylene oxide, with ring-opening, into the compounds of the general formula (Ib)

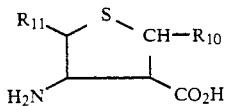
(Ib)

in which
R$^{10}$ and R$^{11}$ have the abovementioned meaning,
or

[C] in the case in which B and B' represent the —SO or —SO$_2$ group,
compounds of the general formula (Ic)

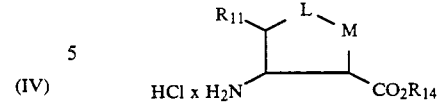
(Ic)

in which
R$^{10}$ and R$^{11}$ have the abovementioned meaning,
R$^{14}$ represents C$_1$-C$_4$-alkyl
and
L and M are different and represent a-sulphur atom or the —CHR$^{10}$ group,
are first oxidised in inert solvents, in the presence of a base, preferably triethylamine, after blocking the free amine function to give the compounds of the general formula (VI)

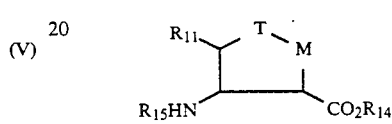
(VI)

in which
M and T are different, and M has the abovementioned meaning and T represents the —SO or —SO$_2$ group,
R$^{10}$, R$^{11}$ and R$^{14}$ have the abovementioned meaning
and
R$^{15}$ represents an amino-protective group known from the literature, preferably tert-butoxycarbonyl (BOC)
with oxidising agents, preferably m-chloroperbenzoic acid, and the protective group is then removed by a customary method, preferably with acids,
and in the case of the acids [(I), (Ia) D, E=O, R$^4$/R$^{4'}$=H] the corresponding esters are optionally hydrolysed,
and in the case of the other definitions mentioned above for D/E and R$^4$/R$^{4'}$, likewise derivatised by customary methods, such as, for example, amidation, sulphonation or sulphoamidation, if appropriate in the presence of auxiliaries such as catalysts and dehydrating agents, starting from the corresponding carboxylic acids, if appropriate with prior activation.

The processes according to the invention can be illustrated by way of example by the following reaction scheme:

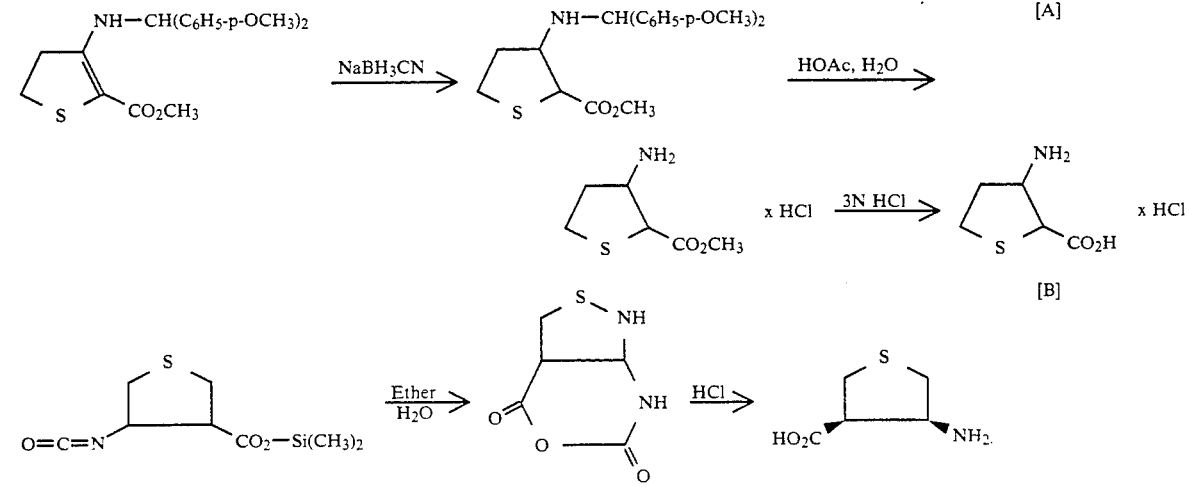

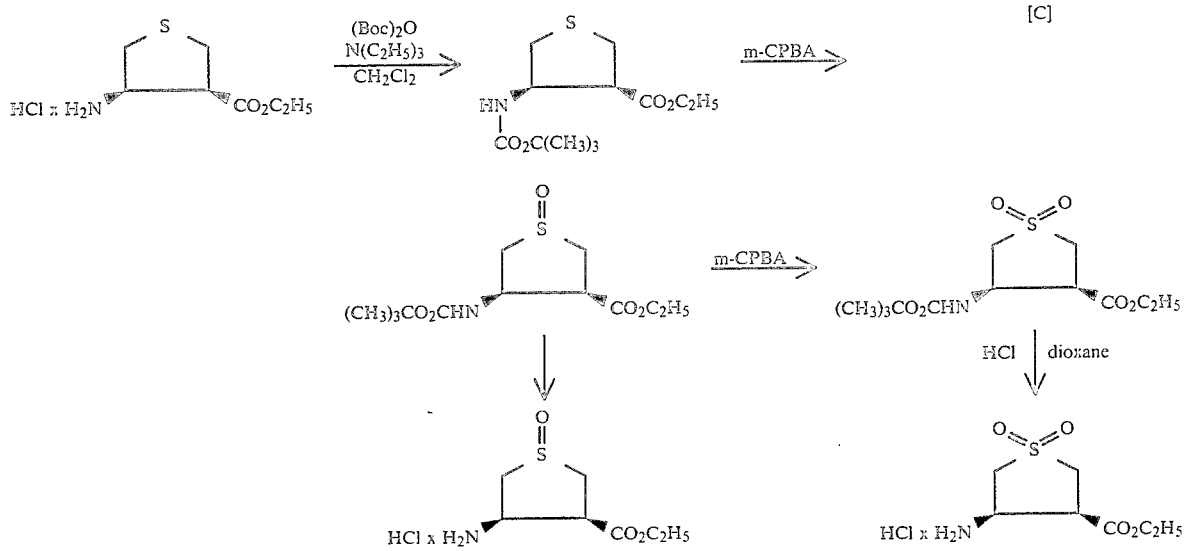

Suitable solvents for processes [A], [B] and [C] are water and all inert organic solvents which do not change under the reaction conditions. These preferably include alcohols such as methanol, ethanol, propanol and isopropanol, ethers such as diethyl ether, dioxane, tetrahydrofuran, glycol monomethyl ether or glycol dimethyl ether, or amides such as dimethylformamide, dimethylacetamide or hexamethylphosphoric triamide, or glacial acetic acid, dimethyl sulphoxide, acetonitrile or pyridine. Those preferred for the individual steps are diethyl ether, dioxane, methanol, ethanol and dichloromethane.

The reaction temperatures can be varied within a relatively wide range. In general, the reaction is carried out between $-78°$ C. and $+150°$ C., preferably between $-10°$ C. and $+100°$ C.

The reactions can be carried out at normal pressure, but also at elevated or reduced pressure (for example 0.5 to 3 bar). In general, the reactions are carried out at normal pressure.

When carrying out process variants [A], [B] and [C] according to the invention, any desired ratio of the substances participating in the reaction can be used. In general, however, the reaction is carried out with molar amounts of the reactants. The substances according to the invention are preferably isolated and purified by distilling off the solvent in vacuo and recrystallising the residue, which may only be obtained in crystalline form after ice-cooling, from a suitable solvent. In some cases, it may be necessary to purify the compounds according to the invention by chromatography.

Suitable oxidising agents are, for example, sodium periodate, peracids such as m-chloroperbenzoic acid or potassium permanganate. m-Chloroperbenzoic acid and sodium periodate are preferred.

Suitable bases are organic amines (trialkyl(C1-C6) amines) such as, for example, triethyla/nine or heterocycles such as pyridine, methylpiperidine, piperidine or morpholine. Triethylamine is preferred.

Acids employed for the ring opening (V) are in general mineral acids. Hydrochloric acid, hydrobromic acid, sulphuric acid and phosphoric acid or else mixtures of the acids mentioned are preferably employed in this case. Hydrochloric acid is preferred.

Suitable acids for the deblocking (III) are $C_1$-$C_6$-carboxylic acids such as, for example, acetic acid or propionic acid. Acetic acid is preferred.

The acid is in general employed in an amount from 2 mol to 30 mol, preferably from 5 mol to 15 mol, in each case relative to 1 mol of the compounds of the general formulae (III) and (V).

The hydrolysis of the carboxylic acid esters is carried out by customary methods by treating the esters in inert solvents with customary bases, it being possible to convert the salts initially formed into the free carboxylic acids by treatment with acid.

The hydrolysis of the carboxylic acid esters can also be carried out with one of the abovementioned acids.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium ethoxide, potassium methoxide or potassium tert-butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from $0°$ C. to $+100°$ C., preferably from $+20°$ C. to $+80°$ C.

In general, the hydrolysis is carried out at normal pressure. However, it is also possible to work at elevated pressure or at reduced pressure (for example from 0.5 to 5 bar).

When carrying out the hydrolysis, the base or the acid is in general employed in an amount from 1 to 3 mol, preferably from 1 to 1.5 mol, relative to 1 mol of the ester. Molar amounts of the reactants are particularly preferably used.

When carrying out the reaction, in the first step the salts of the compounds according to the invention are formed as intermediates which can be isolated. The acids according to the invention are obtained by treating the salts with customary inorganic acids. These preferably include mineral acids such as, for example, hydrochloric acid, hydrobromic acid, sulphuric acid or phosphoric acid. It has proved advantageous in the preparation of the carboxylic acids to acidify the basic reaction mixture from the hydrolysis in a second step without isolation of the salts. The acids can then be isolated in a customary manner.

Amino-protective groups in the context of the invention are the customary amino-protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert.-bdtoxycarbonyl, allyloxycarbonyl, vinyloxycarbonyl, 2-nitrobenzyloxycarbonyl, 3,4,5-trimethoxybenzyloxycarbonyl, cyclohexylcarbonyl, 1,1-dimethylethoxycarbonyl, adamantylcarbonyl, phthaloyl, 2,2,2-trichloroethoxycarbonyl, 2,2,2-trichloro-tert.-butoxy-carbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl.

As an example of the abovementioned derivatisation possibilities, amidation and sulphonation or sulphoamidation will be illustrated here.

Amidation is in general carried out in inert solvents in the presence of a base and of a dehydrating agent.

Suitable solvents in this case are inert organic solvents which do not change under the reaction conditions. These include halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or mineral oil fractions, nitromethane, 3nethylformamide, acetonitrile or hexamethylphosphoric triamide. It is also possible to employ mixtures of the solvents. Dichloromethane is particularly preferred.

Suitable bases for the amidation are the customary basic compounds. These preferably include alkali metal and alkaline earth metal hydroxides such as lithium hydroxide, sodium hydroxide, potassium hydroxide or barium hydroxide, alkali metal hydrides such as sodium hydride, alkali metal or alkaline earth metal carbonates such as sodium carbonate or potassium carbonate, or alkali metal alkoxides such as, for example, sodium methoxide or ethoxide, potassium ethoxide or ethoxide or potassium tert-butoxide, or organic amines such as benzyltrimethylammonium hydroxide, tetrabutylammonium hydroxide, pyridine, triethylamine or N-methylpiperidine.

The amidation is in general carried out in a temperature range from 0° C. to 150° C., preferably at 25° C. to 40°C.

The amidation is in general carried out at normal pressure. However, it is also possible to carry out the process at reduced pressure or at elevated pressure (for example in a range from 0.5 to 5 bar).

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazoliumcompounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulfonyl chloride, if appropriate in the presence of bases such as triethylamine or N-ethylmorpholine or N-methylpiperidine or dicyclohexylcarbodiimide and N-hydroxysuccinimide [cf. J. C. Sheehan, S. L. LEdis, J. Am. Chem. Soc. 95, 875 (1973); F. E. Fretman et al., J. Biol. Chem. 255, No. 5, 2199–2202 (1980) and N. B. Benoton, K. Kluroda, Int. Pept. Prot. Res. 13, 403 (1979), 17, 187 (1981)].

The sulphonation or sulphoamidation is carried out in the abovementioned inert solvents, if appropriate using the bases and dehydrating agents likewise mentioned above.

The sulphonation and sulphoamidation are in general carried out at normal pressure. However, it is also possible to carry out the processes at reduced pressure or elevated pressure (for example in a range from 0.5 to 5 bar).

The sulphonation and the sulphoamidation are in general carried out in a temperature range from 0° C. to +150° C., preferably from +25° C. to +40°C.

For the amidation, the commercially available amines and their derivatives known from the literature are in general suitable [cf. Houben-Weyl, "Methoden der organischen Chemie" (Methods of organic chemistry), Vol. XI/1 and XI/2].

The sulphonation and sulphoamidation are in general also carried-out with the customary sulphonic acids and their activated derivatives [cf. Houben-Weyl, "Methoden der organischen Chemie" (Methods of organic chemistry), Vol IX, p. 407 et seq.; Beilstein 11, 26].

The esterification of the acids is carried out by a customary method by reacting the acids, if appropriate in one of the abovementioned solvents, with the appropriate alcohols in the presence of a catalyst. Preferably, this alcohol is also employed as the solvent.

Catalysts which can be employed are inorganic acids, such as, for example, sulphuric acid or inorganic acid chlorides, such as, for example, thionyl chloride.

In general, 0.01 to 1, preferably 0.05 to 0.5, mol of catalyst are employed, relative to 1 mol of reactant.

Both the esterification and the amidation can optionally proceed via activated stages of the carboxylic acids, such as, for example, acid halides, which can be prepared from the corresponding acid by reaction with thionyl chloride, phosphorus trichloride, phosphorus pentachloride, phosphorus tribromide or oxalyl chloride.

The acid addition salts of the compounds of the formula (I) can be obtained in a simple manner by customary salt formation methods, for example by dissolving a compound of the formula (I) in a suitable solvent and adding the acid, for example hydrochloric acid, and isolated in a known manner, for example by filtering off, and if appropriate purified by washing with an inert solvent.

The compounds of the general formula (II) are new and can be prepared by a process in which compounds of the general formula (VII)

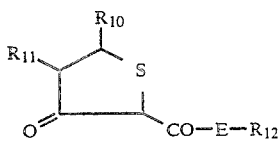

in which $R^{10}$, $R^{11}$, $R^{12}$ and E have the abovementioned meaning, are reacted with 4,4'-dimethoxy-benzhydrylamine in one of the abovementioned solvents, preferably benzene, in the presence of p-toluenesulphonic acid.

The compounds of the general formula (VII) are known in some cases or are new and can then be prepared, however, in analogy to processes known from the literature.

The compounds of the general formula (III) are new and can be prepared by the abovementioned process.

The compounds of the general formula (IV) are new and can be prepared by a process in which compounds of the general formula (VIII)

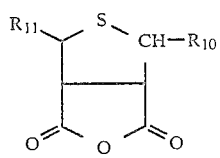

in which $R^{10}$ and $R^{11}$ have the abovementioned meaning, are reacted with compounds of the general formula (IX)

$$(R^{13})_4 SiN_3 \quad (IX)$$

in which

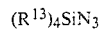

$R^{13}$ has the abovementioned meaning, in a temperature range from $+20°$ C. to $+80°$ C., preferably at 80° C.

The compounds of the general formula (VIII) are known in some cases, in particular the unsubstituted cis-isomer, or are new and can then be prepared, however, via the corresponding dicarboxylic acids by dehydration in analogy to known processes [cf. J. Org. Chem. 12, 174 (1947)].

The compounds of the general formula (IX) are known [cf. Fieser 1, 1236; 3, 316; 5, 719; 6, 632; 7, 394; 9, 21; 10, 14].

The compounds of the general formula (V) are new and can be prepared by the abovementioned process.

With the exception of the cis-isomer [cf. J. Org. Chem. 12, 174 (1947)], the compounds of the general formula (Ib) are new and can be prepared as described in [B].

The compounds of the general formula (VI) are known in some cases [cf. Bull. Chem. Soc. Jpn. 40 (11), 2636-40; Chem. Bet. 123 (1990), 1999-2014], other ester groupings optionally being present, or are new and can then be prepared, however, by the method indicated in the abovementioned literature reference.

The compounds of the general formula (Ic) are new and can be prepared by the abovementioned process.

The above preparation processes are only given for clarification. The preparation of the compounds of the general formulae (I) and (Ia) according to the invention is not restricted to these processes, and any modification of these processes can be used in the same manner for the preparation.

The compounds of the general formulae (I) and (Ia) according to the invention and their acid addition salts have antimicrobial actions, in particular potent antimycotic actions. They have a very broad spectrum of antimycotic action, in particular against dermatophytes and budding fungi as well as biphasic fungi, for example against Candida species such as Candida albicans, Epidermophyton species such as *Epidermophyton floccosum,* Aspergillus species such as *Aspergillus niger* and *Aspergillus fumigatus,* Trichophyton species such as *Trichophyton mentagrophites,* Microsporon species such as *Microsporon felineum* and Torulopsis species, such as *Torulopsis glabrata.* The enumeration of these microorganisms in no way represents a restriction of the microorganisms which can be controlled, but is of only illustrative character.

Indication examples which may be mentioned in human medicine are, for example: Dermatomycoses and systemic mycoses caused by Trichophyton mentagrophytes and other Trichophyton species, Microsporon species and *Epidermophyton floccosum,* budding fungi and biphasic fungi as well as mould fungi.

Indication areas in veterinary medicine which may be mentioned are, for example: All dermatomycoses and systemic mycoses, in particular those which are caused by the abovementioned pathogens.

The compounds according to the invention were tested for their antimycotic in vivo activity in the mouse candidiasis model in the i.v., s.c. and oral administration modes: Male $CF_1$-SPF mice were infected with $1-3 \times 10^6$ budding cells of C. albicans per animal by injection of the microorganism suspension in physiological NaCl solution (0.2 ml/animal) into the tail vein. Under these infection conditions, untreated control animals develop renal candidiasis and up to 95–100% of the animals employed die within 6 days post-infection of this infection. If infected animals are treated twice daily, starting with the day of infection, with the compounds according to the invention orally or parenterally in doses of $2 \times 25$ to $2 \times 50$ mg/kg of body weight over the course of 2–5 days, 60–90% of the animals survive the infection in good condition. The numbers of *C. albicans* microorganisms in the kidneys of the infected and treated animals on the 4th day post-infection are on average 2 powers of ten below those of untreated, infected control animals.

In the following table, the in vivo actions of some compounds according to the invention in the mouse candidiasis model are shown:

TABLE A

| Example No. | Dose mg/kg | Type of administration | Number of surviving animals on the 6th day post-infection |
|---|---|---|---|
| Control | — | — | 1/10 |
| 2 | 25 | s.c., i.v. | 7/10 |
| 3 | 25 | s.c., oral | 9/10 |
| 9 | 25 | s.c. | 7/10 |
| 11 | 25 | s.c. | 8/10 |

Under conventional test conditions—serial dilution test and agar diffusion test—the compounds are not antianycotically active in vitro.

The new active substances can be converted in a known manner into the customary formulations, such as tablets, coated tablets, pills, granules, aerosols, syrups, emulsions, suspensions and solutions, using inert, non-toxic, pharmaceutically suitable excipients or solvents. In this case the therapeutically active compound should in each case be present in a concentration of about 0.5 to 90% by weight of the total mixture, i.e. in amounts which are sufficient in order to achieve the dosage range indicated.

The formulations are prepared, for example, by extending the active substances with solvents and/or excipients, if appropriate using emulsifiers and/or dispersants, where, for example, in the case of the use of water as a diluent organic solvents can optionally be used as auxiliary solvents.

Administration is carried out in a customary manner, preferably orally or parenterally, in particular perlingually or intravenously.

In the case of parenteral use, solutions of the active substance can be employed using suitable liquid excipients.

In general, it has proved advantageous on intravenous administration to administer amounts of about 0,001 to 10 mg/kg, preferably about 0.01 to 5 mg/kg, of body weight to achieve effective results, and on oral administration the dosage is about 0.01 to 25 mg/kg, preferably 0.1 to 10 mg/kg, of body weight.

In spite of this it may sometimes be necessary to deviate from the amounts mentioned, in particular depending on the body weight or the type of application route, on individual behavior towards the medicament, the manner of its formulation and the time or interval at which administration takes place. Thus, in some cases it may be adequate to manage with less than the above-mentioned minimum amount, while in other cases the upper limit mentioned must be exceeded. In the case of the administration of relatively large amounts, it may be advisable to divide these into several individual doses over the course of the day.

STARTING COMPOUNDS

Example I

Trimethylsilyl 3,4-cis-4-isocyanato-tetrahydro-3-thiophenecarboxylate

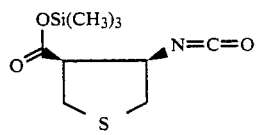

A solution of thiophane-3,4-cis-dicarboxylic anhydride (10.0 g; 63.2 mmol) and trimethylsilyl azide (8.29 g, 72.0 mmol) in 60 ml of dioxane is heated to 80° C. for 2 h. The solvent is stripped off in vacuo and the residue is distilled in a bulb tube.

Yield: 9.30 g (63% of theory).
B.p., 160–170° C./0.4 mm Hg.
C$_8$H$_{15}$NO$_3$SSi(233.36).
$^1$H-NMR (CDCl$_3$):δ=0.33 (s, 9H); 2.93–3.28 (m, 5H); 4.53–4.59 (m, 1H).

Example II 4a,5,7,7a-tetrahydro-thieno[3,4-d]oxazine-2,4(1H)-dione

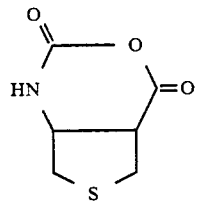

A solution of the compound from Example I (7.30 g, 31.3 mmol) in 45 ml of diethyl ether is mixed with water (0.28 g, 15.6 mmol) and allowed to stand at 6° C. for 2h. Precipitated product is filtered off and washed with diethyl ether.

Yield: 3.30 g (62% of theory).
C$_6$H$_{17}$NO$_3$S(173.2).
IR (KBr) max: 1811, 1727 cm$^{-1}$.

Example III

Ethyl 3,4-cis-4-N-(tert-butoxycarbonyl)amino-tetrahydro-3-thiophene-carboxylate

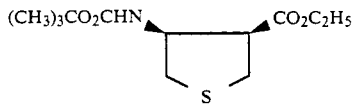

A solution of the compound from Example I (5.0 g, 24 mmol) and triethylamine (7.1 g, 72 mmol) in 60 ml of dichloromethane is mixed with di-tert-butyl dicarbonate (7.9 g, 36 mmol) and stirred at room temperature for 20 h. The solvent is stripped off in vacuo and the residue is chromatographed on silica gel (ether/petroleum ether =1:2).

Yield: 5.9 g (95% of theory).
C$_{12}$H$_{21}$NO$_4$S(259.4).
M.p.: 67° C.

Example IV

Ethyl 3,4-cis-4-N-(tert-butoxycarbonyl)amino-tetrahydro-3-thiophene-carboxylate-1-oxide

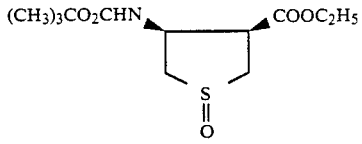

A solution of m-chloroperbenzoic acid (3.10 g, 12.7 mmol) in 30 ml of dichloromethane is added dropwise at −78° C. to the solution from Example III (3.30 g, 12.7 mmol) in 60 ml of dichloromethane. The mixture is allowed to warm to 0° C. and is mixed, with stirring, with 150 ml of a 10% strength aqueous sodium bisulphite solution, and the phases are separated. The organic phase is washed twice with saturated aqueous NaHCOa solution and dried over sodium sulphate. The solvent is stripped off in vacuo.

Yield: 2.70 g (77% of theory).
C$_{12}$H$_{21}$NO$_5$S(291.4).

M.p.: 115°–120° C.
Diastereomer ratio $D_1:D_2 = 2.2:1$.

Example V

Ethyl 3,4-cis-4-N-(tert-butoxycarbonyl)amino-tetrahydro-3-thiophene-carboxylate-1,1-dioxide

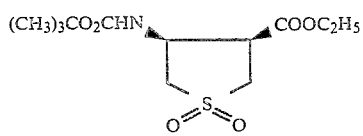

m-Chloroperbenzoic acid (1.00 g, 4.1 mmol) is added at 0° C. to a solution of the compound from Example III (1.20 g, 4.1 mmol) in 20 ml of dichloromethane and the mixture is stirred at room temperature for 5 h. It is mixed with stirring with 20 ml of a 20% strength aqueous sodium bisulphite solution and the phases are separated. The organic phase is washed twice with saturated NaHCO$_3$ solution and dried over sodium sulphate. The solvent is stripped off in vacuo and the residue is recrystallised from ethyl acetate.

Yields 0.93 g (74% of theory).
$C_{12}H_{12}NO_6S(307.4)$,
M.p.s 128° C.

Example VI

Methyl 3-N-(4,4'-dimethoxybenzhydryl)amino-4,5-dihydro-thiophene-2-carboxylate

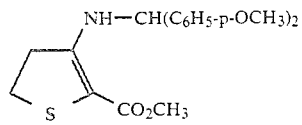

A solution of 4.5 g (28.0 nunol) of methyl tetrahydrothiophene-3-one-2-carboxylate, 6.9 g (28 mmol) of 4,4'-dimethoxy-benzhydrylamine and 0.1 g of p-toluenesulphonic acid are heated under reflux in a water separator in 50 ml of benzene for 24 h. The mixture is then diluted with 40 ml of toluene, and washed with 40 ml of 1% strength aqueous NaHCO$_3$ solution and twice with 30 ml of water in each case. The organic phase is dried over Na$_2$SO$_4$ and the solvent is stripped off in vacuo. The residue is chromatographed on silica gel (ether/petroleum ether =1:2)

Yield: 7.58 g (70% of theory).
$C_{21}H_{23}NO_4S(385.4)$.
R$_f$=0.42 (ether: petroleum ether =1:2).

Example VII

Methyl 3-N-( 4,4'-dimethoxybenzhydryl ) amino-tetrahydrothiophene- 2-carboxylate

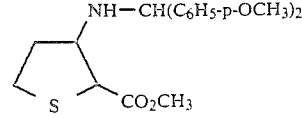

A solution of 0.50 g (1.30 nunol) of the compound from Example VI in 10 ml of ethanol is mixed with 0.080 g (1.30 nunol) of sodium cyanoborohydride and then with 6 N HCl until the indicator of Bromocresol Green turns yellow. It is stirred at room temperature for 24 h, the solvent is stripped off in vacuo and the residue is mixed with 10 ml of ether acetate. The solution is washed with 10 ml of 1% strength aqueous NaHCO$_3$ solution and with 10 ml of water and dried over Na$_2$SO$_4$. The residue is chromatographed on silica gel (ether: petroleum ether =1:2)

Yield: 0.32 g (64% of theory),
$C_{21}H_{25}NO_4S(387.5)$.
R$_f$=0.34 (ether: petrol ether =1:2).

Example VIII and IX

Methyl 3-N-(tert-butoxycarbonyl)amino-tetrahydro-2-thiophene-carboxylate

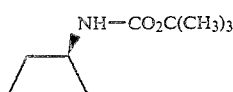 (VIII)

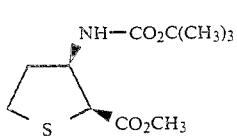 (IX)

A solution of Example 8 (9.45 g; 58.6 mmol) in 150 ml of dichloromethane is mixed with triethylamine (17.3 g; 176 mmol) and then with di-tert-butyl dicarbonate (19.3 g; 87.9 mmol) and stirred at room temperature for 20 h. The solvent is stripped off in vacuo and the residue is chromatographed on silica gel (ether/petroleum ether =1:2).

Diastereomer (VIII):
Yield: 8.76 g (57%).
R$_f$=0.43 (ether/petroleum ether=1:2), M.p.: 93° C.
Diastereomer (IX):
Yield: 4.08 g (19%).
R$_f$=0.35 (ether/petroleum ether=1:2), M.p.: 69° C.
$C_{11}H_9NO_4S(261.34)$.

Example X

Methyl 3-N-(tert-butoxycarbonyl)amino-tetrahydro-2-thiophene-carboxylate-1-oxide

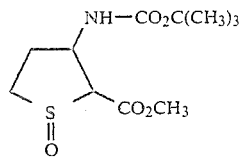

A solution of m-chloroperbenzoic acid ( 2.80 g; 11.4 mmol) in 30 ml of dichloromethane is added dropwise at −78° C. to a solution of Example VIII (3.0 g; 11.4 mmol) in 60 ml of dichloromethane. The mixture is allowed to warm to 0° C. and is mixed with stirring with 150 ml of a 10% strength sodium bisulphite solution, and the phases are separated. The organic phase is washed twice with saturated aqueous NaHCO$_3$ solution and dried over Na$_2$SO$_4$. The solvent is stripped off in vacuo.

Yield: 2.50 g (79% of a diastereomeric mixture).
$C_{11}H_{19}NO_5S(277.3)$.
M.p.: 110–115° C.

Example XI

Methyl 3-N-(tert-butoxycarbonyl)amino-tetrahydro-2-thiophene-carboxylate-1,1-dioxide

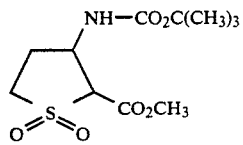

m-Chloroperbenzoic acid (5.60 g; 22.8 mmol) is added at −50° C. to a solution of Example VIII (3.0 g; 11.4 mmol) in 90 ml of $CH_2Cl_2$, and the mixture is allowed to warm to room temperature and stirred at this temperature for a further 5 h. The mixture is mixed with stirring with 150 ml of a 10% strength sodium bisulphite solution and the phases are separated. The organic phase is washed twice with saturated aqueous $NaHCO_3$ solution and dried over $Na_2SO_4$. The solvent is stripped off in vacuo.

Yield: 2.40 g (72% of a diastereomeric mixture).
$C_{11}H_{19}NO_6S$ (293.3).
M.p.: 95°–98° C.

PREPARATION EXAMPLES

Example 1

Ethyl 3,4-cis-4-amino-tetrahydro-3-thiophenecarboxylate hydrochloride

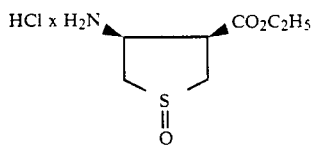

A solution of the compound from Example II (3.00 g, 17.3 mmol) in 35 ml of ethanol is mixed at −10°−0° C. with acetyl chloride (2.20 g, 28.0 mmol), stirred at room temperature for 20 h, concentrated in vacuo to a volume of about 8 ml and mixed with 6 ml of ether, and precipitated product is filtered off.

Yield: 2.60 g (72% of theory).
$C_7H_{13}NO_2S \times HCl$.
Melting point: 100° C.

Example 2

3,4-cis-4-Amino-tetrahydro-3-thiophenecarboxylic acid hydrochloride

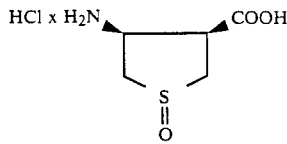

A solution of the compound from Example 1 (0.800 g, 3.80 mmol) in 55 ml of 20% strength aqueous HCl solution is heated under reflux for 2 h and then evaporated to dryness in vacuo.

Yield: 0.67 g (97% of theory).
$C_5H_9NO_2S \times HCl$.
Melting point: 205°–210° C.

Example 3

Methyl 3,4-cis-4-amino-tetrahydro-3-thiophene-carboxylate hydrochloride

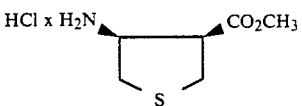

A solution of the compound from Example II (0.60 g, 3.46 mmol) in 10 ml of methanol is mixed at −10° C.−0° C. with acetyl chloride (0.44 g, 5.60 mmol), stirred at room temperature for 20 h, concentrated in vacuo to a volume of about 2 ml and mixed with 3 ml of ether. Precipitated product is filtered off.

Yield: 0.30 g (46% of theory).
$C_6H_{11}NO_2S \times HCl$.
Melting point: 168° C.

Example 4

Ethyl 3,4-cis-4-amino-tetrahydro-3-thiophene-carboxylate-1-oxide hydrochloride

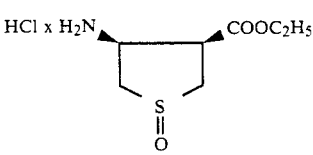

A solution of the compound from Example IV (2.00 g, 7.26 mmol) in 10 ml of a 4N solution of HCl in 1,4-dioxane is stirred at room temperature for 5 h. Precipitated product is filtered off with suction, washed with ether and dried in vacuo.

Yield: 0.71 g (44% of theory).
$C_7H_{13}NO_3S \times HCl$.
Melting point: 98° C.
Diastereomer ratio $D_1: D_2 = 2.2:1$.

Example 5

3,4-cis-4-Amino-tetrahydro-3-thiophene-carboxylic acid-1-oxide hydrochloride

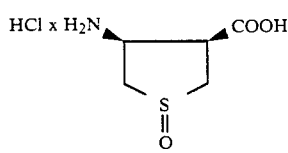

A solution of the compound from Example 4 (0.35 g, 1.54 mmol) in 30 ml of 3 N HCl is heated under reflux for 2 h. The solution is concentrated in vacuo and the residue is dried in vacuo at 50° C./0.1 mm Hg.

Yield: 0.30 g (96% of theory).
$C_5H_9NO_3S \times HCl$
MS(FAB): m/z = 164 $(M+H)^+$.
Diastereomer ratio $D_1:D_2 = 2.2:1$.

Example 6

Ethyl 3,4-cis-4-amino-tetrahydro-3-thiophene-carboxylate-1-dioxide hydrochloride

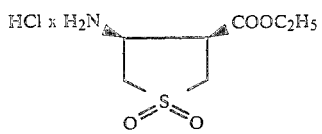

A solution of the compound from Example V (1.00 g, 3.30 mmol) in 5 ml of 4 N HCl in dioxane is stirred at room temperature for 3 h. The solvent is stripped off in vacuo and the residue is dried in vacuo at 0.1 mm Hg/50° C.

Yield: 0.80 g (100% of theory).
$C_7H_{13}NO_4S \times HCl$.
M.p.: 150°155° C.

Example 7

3,4-cis-4-Amino-tetrahydro-3-thiophene-carboxylic acid-1,1-dioxide hydrochloride

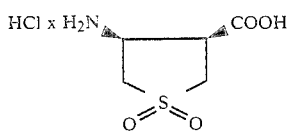

A solution of the compound from Example 6 (0.50 g, 2.0 mmol) is heated under reflux in 20 ml of 3 N HCl for 2 h. The solution is concentrated in vacuo and the residue is dried in vacuo at 50° C./0.1 mmHg.

Yield: 0.44 (100% of theory).
$C_5H_9NO_4S \times HCl$.
M.p.: 212° C.

Example 8

Methyl 3-amino-tetrahydrothiophene-2-carboxylate hydrochloride

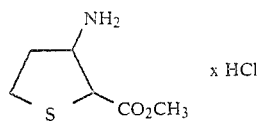

A solution of 0.48 g (1.24 mmol) of the compound from Example VII in 10 ml of acetic acid/water (1:1) is heated at 80° C. for 5 min. It is diluted with 20 ml of water and extracted twice with 10 ml of ether each time. The aqueous phase is concentrated in vacuo at 20° C., and the residue is taken up in 5 ml of water and mixed with conc. $NH_3$ until the pH is 10. It is extracted three times with 10 ml of ether each time. The ether phases are dried over $Na_2SO_4$ and the solvent is stripped off in vacuo. The residue is mixed with 1 ml of 2N methanolic HCl and the solvent is stripped off in vacuo. The residue is dried in vacuo at 0.1 mmHg/50° C.

Yield: 0.124 g (51% of theory), $C_6H_{11}NO_2S \times HCl$ $R_f=0.45$ (ether: acetonitrile: conc. $NH_3=10:1:0.1$). Diastereomer ratio 3:1.

Examples 9 and 10

Methyl 3-amino-tetrahydrothiophene-2-carboxylate hydrochloride

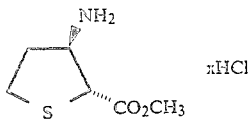 (9)

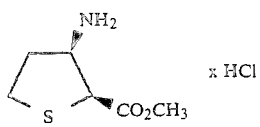 (10)

A solution of 1.50 g (5.74 mmol) of the compounds from Examples VIII and IX in 9 ml of 4N HCl in dioxane is stirred at room temperature for 3 hours. Precipitated product is filtered off with suction, washed with ether and dried.

Diastereomer (9):
Yield: 1.14 g (100%).
M.p.: 146° C.
$C_6H_{11}NO_2S \times HXl$.

Diastereomer (10):
Yield: 0.99 g (87%).
M.p.: 172° C.
$C_6H_{11}NO_2S \times HCl$.

Examples 11 and 12

3-amino-tetrahydrothiophene-2-carboxylic acid hydrochloride

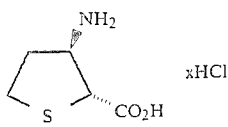 (11)

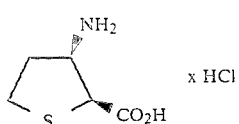 (12)

A solution of 0.50 g (2.5 mmol) of the compounds from Examples 9 and 10 in 25 ml of 3 N HCl is heated under reflux for 3 h. The solvent is stripped off in vacuo and the residue is dried at 0.1 mm Hg/50° C.

Diastereomer (11):
Yield: 0.41 g (89%).
M.p.: 231° C.

Diastereomer (12):
Yield: 0.42 g (91%).
M.p.: 160° C.
$C_5H_9NO_2S \times HCl$.

Example 13

Methyl 3-amino-tetrahydrothiophene-2-carboxylate-1,1-dioxide hydrochloride

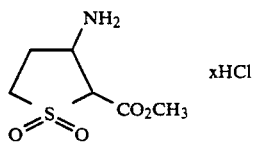

A solution of Example XI (3.50 g; 12.0 mmol) in 20 ml of 4 N HCl in dioxane is stirred at room temperature for 3 h. The solvent is stripped off in vacuo and the residue is washed with tetrahydrofuran.

Yield: 1.46 g (77% of a diastereomeric mixture).
$C_6H_{11}NO_4S \times HCl$ (193.2 × 36.5).
M.p.: >250° C.

Example 14

3-Amino-tetrahydrothiophene-2-carboxylic acid-1,1-dioxide hydrochloride

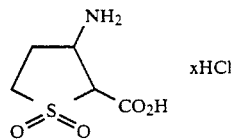

A solution of Example 13 (1.0 g; 4.4 mmol) in 30 ml of strength hydrochloric acid is heated under reflux for 2 h. The solvent is stripped off in vacuo and the residue is washed with tetrahydrofuran.

Yield: 0.22 g (23% of a diastereomeric mixture).
$C_5H_9NO_4S \times HCl$ (179.2 × 36.5).
M.p.: >250° C.

We claim:

1. A fungicidal composition comprising a substituted tetrahydrothiophene of the general formula (I)

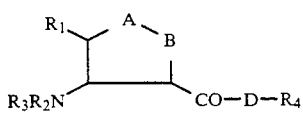

in which
  A and B are always different and represent a sulphur atom or the group of the formula —$CHR^5$,
  in which
  $R^5$ denotes hydrogen or straight-chain or branched alkyl having up to 8 carbon atoms, which is optionally substituted by halogen, hydroxyl, phenyl or carboxyl or alkoxy carbonyl each having up to 6 carbon atoms,
  $R^1$ represents hydrogen or straight-chain or branched alkyl having up to 8 carbon atoms, which is optionally substituted 1 or 2 times by identical or different substituents from the series comprising halogen, hydroxyl, phenyl and carboxyl or by straight-chain or branched alkoxy, acyl or alkoxycarbonyl each having up to 6 carbon atoms or by a group of the formula —$NR^6R^7$,
  in which $R^6$ and $R^7$ are identical or different and denote hydrogen, phenyl or straight-chain or branched alkyl having up to 6 carbon atoms,
  $R^2$ represents hydrogen or
  represents straight-chain or branched alkyl having up to 8 carbon atoms, which is optionally substituted 1 or 2 times by identical or different substituents from the series comprising hydroxyl and formyl or by straight-chain or branched acyl having up to 6 carbon atoms or by phenyl or benzoyl, each of which is optionally substituted up to 2 times by identical or different substituents from the series comprising halogen, nitro and cyano, or by straight-chain or branched alkyl having up to 6 carbon atoms,
  or
  represents straight-chain or branched acyl having up to 8 carbon atoms,
  or
  represents benzoyl which is optionally substituted as described above,
  or
  represents a group of the formula —$SO_2R^8$,
  in which
  $R^8$ denotes straight-chain or branched alkyl having up to 8 carbon atoms, or benzyl or phenyl, where the latter are optionally substituted up to 3 times by identical or different substituents from the series comprising halogen, hydroxyl, nitro, cyano, trifluoromethyl and trifluoromethoxy or by straight-chain or branched alkyl, alkoxy or alkoxycarbonyl each having up to 6 carbon atoms, carboxyl or by the abovementioned group —$NR^6R^7$,
  in which
  $R^6$ and $R^7$ have the abovementioned meaning,
  represents phenyl which is optionally substituted up to 3 times by identical or different substituents from the series comprising halogen, hydroxyl, nitro, trifluoromethyl, trifluoromethoxy, straight-chain or branched alkyl, acyl, and alkoxy or alkoxycarbonyl each having up to 6 carbon atoms or by a group of the formula —$NR^6R^7$ or —$SO_2R^8$,
  in which
  $R^6$, $R^7$ and $R^8$ have the abovementioned meaning,
  $R^3$ represents hydrogen or straight-chain or branched alkyl having up to 8 to carbon atoms, which is optionally substituted by phenyl,
  or
  $R^2$ and $R^3$ together represent the radical of the formula =$CHR^{5'}$,
  in which
  $R^{5'}$ denotes hydrogen or straight-chain or branched alkyl having up to 8 carbon atoms, which is optionally substituted by halogen, hydroxyl, henyl or carboxyl or by straight-chain or branched alkoxy or alkoxy carbonyl each having up to 6 carbon atoms,
  D represents an oxygen or sulphur atom or the

group,
  $R^4$ represents hydrogen or straight-chain or branched alkyl having up to 8 carbon atoms, or phenyl, where the latter are optionally substituted up to 3 times by identical or different substituents from the group comprising hydroxyl, halogen, nitro, cyano, carboxyl, trifluoromethyl and trifluoromethoxy, by straight-chain or branched alkoxy, in the case of phenyl also by alkyl, acyl or alkoxycarbonyl each having up to 6 carbon atoms or by a group of the formula —NR$^6$R$^7$ or —SO$_2$R$^8$, in which R$^6$, R$^7$ and R$^8$ have the abovementioned meaning, or for the case in which D represents the

group
R$^4$ represents the group of the formula —SO$_2$R$^8$,
in which
R$^8$ has the abovementioned meaning.

2. A fungicidal composition comprising a substituted tetrahydrothiophene of the general formula (Ia)

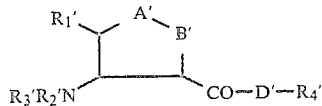

in which
A' and B' are always different and represent a sulphur atom or the group of the formula —CHR$^9$,
in which
R$^9$ denotes hydrogen or straight-chain or branched alkyl having up to 8 carbon atoms, which is optionally substituted by halogen, hydroxyl, phenyl or carboxyl or by straight-chain or branched alkoxy or alkoxy carbonyl each having up to 6 carbon atoms,
R$^{1'}$ represents hydrogen or straight-chain or branched alkyl having up to 8 carbon atoms, which is optionally substituted 1 or 2 times by identical or different substituents from the series comprising halogen, hydroxyl, phenyl or carboxyl or by straight-chain or branched alkoxy, acyl or alkoxy carbonyl each having up to 6 carbon atoms or by a group of the formula —NR$^{6'}$R$^{7'}$,
in which
R$^{6'}$ and R$^{7'}$ are identical or different and denote hydrogen, phenyl or straight-chain or branched alkyl having up to 6 carbon atoms,
R$^{2'}$ represents hydrogen or
represents straight-chain or branched alkyl having up to 8 carbon atoms, which is optionally substituted 1 or 2 times by identical or different groups from the series comprising hydroxyl and formyl or by straight-chain or branched acyl having up to 6 carbon atoms or by phenyl or benzoyl, each of which is optionally substituted up to 2 times by identical or different substitutents from the series comprising halogen, nitro and cyano, or by straight-chain or branched alkyl having up to 6 carbon atoms, or represents straight-chain or branched acyl having up to 8 carbon atoms, or
represents benzoyl which is optionally substituted as described above, or represents a group of the formula —SO$_2$R$^{8'}$,
in which
R$^{8'}$ denotes straight-chain or branched alkyl having up to 8 carbon atoms, benzyl or phenyl, where the latter are optionally substituted up to 3 times by identical or different substituents from the series comprising halogen, hydroxyl, nitro, cyano, trifluoromethyl and trifluoromethoxy or by straight-chain or branched alkyl, alkoxy or alkoxycarbonyl each having up to 6 carbon atoms, carboxyl or by the abovementioned group —NR$^{6'}$R$^{7'}$,
in which
R$^{6'}$ and R$^{7'}$ have the abovementioned meaning,
represents phenyl which is optionally substituted up to 3 times by identical or different substituents from the series comprising halogen, hydroxyl, nitro, trifluoromethyl, trifluoromethoxy and straight-chain or branched alkyl, acyl, alkoxy or alkoxycarbonyl each having up to 6 carbon atoms or by a group of the formula —NR$^{6'}$R$^{7'}$ or —SO$_2$R$^{8'}$,
in which
R$^{6'}$, R$^{7'}$ and R$^{8'}$ have the abovementioned meaning,
R$^{3'}$ represents hydrogen or straight-chain or branched alkyl having up to 8 carbon atoms, which is optionally substituted by phenyl,
or
R$^{2'}$ and R$^{3'}$ together represent the radical of the formula =CHR$^{9'}$,
in which
R$^{9'}$ has the abovementioned meaning of R$^9$ and is identical to or different from this,
D' represents an oxygen or sulphur atom or the

group, R$^{4'}$ represents hydrogen or straight-chain or branched alkyl having up to 8 carbon atoms or phenyl, where the latter are optionally substituted up to 3 times by identical or different substituents from the series comprising hydroxyl, halogen, nitro, cyano, carboxyl, trifluoromethyl and rifluoromethoxy, by straight-chain or branched alkoxy, in the case of phenyl also by alkyl, acyl or alkoxycarbonyl each having up to 6 carbon atoms or by a group of the formula —NR$^{6'}$R$^{7'}$ or —SO$_2$R$^{8'}$,
in which
R$^{6'}$, R$^{7'}$ and R$^{8'}$ have the abovementioned meaning, or for the case in which D represents the

group,
R$^{4'}$ represents the group of the formula —SO$_2$R$^{8'}$,
in which
R$^{8'}$ has the abovementioned meaning,
with the proviso that if A' represents a sulphur atom, B' represents the —CH$_2$— group, D' represents an oxygen atom and R$^{1'}$, R$^{2'}$, and R$^{3'}$ and R$^{4'}$ represent hydrogen, the two substituents —NR$^{2'}$R$^{3'}$ and —CO—D'—R$^{4'}$ must not both be present in the trans-position.

3. A method of treating fungal diseases in a host in need thereof, by administering substituted tetrahydrothiophenes of the general formula (I)

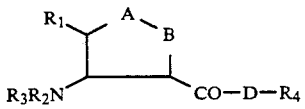

in which

A and B are always different and represent a sulphur atom or the group of the formula —CHR$^5$, in which R$^5$ denotes hydrogen or straight-chain or branched alkyl having up to 8 carbon atoms, which is optionally substituted by halogen, hydroxyl, phenyl or carboxyl or by straight-chain or branched alkoxy or alkoxy carbonyl each having up to 6 carbon atoms, R$^1$ represents hydrogen or straight-chain or branched alkyl having up to 8 carbon atoms, which is optionally substituted 1 to 2 times by identical or different substituents from the series comprising halogen, hydroxyl, phenyl and carboxyl or by straight-chain or branched alkoxy, acyl or alkoxycarbonyl each having up to 6 carbon atoms or by a group of the formula —NR$^6$R$^7$, in which R$^6$ and R$^7$ are identical or different and denote hydrogen, phenyl or straight-chain or branched alkyl having up to 6 carbon atoms, R$^2$ represents hydrogen or represents straight-chain or branched alkyl having up to 8 carbon atoms, which is optionally substituted 1 to 2 times by identical or different substituents from the series comprising hydroxyl and formyl or by straight-chain or branched acyl having up to 6 carbon atoms or by phenyl or benzoyl, each of which is optionally substituted up to 2 times by identical or different substituents rom the series comprising halogen, nitro and cyano, or by straight-chain or branched alkyl having up to 6 carbon atoms, or represents straight-chain or branched acyl having up to 8 carbon atoms, or represents benzoyl which is optionally substituted as described above, or represents a group of the formula —SO$_2$R$^8$, in which R$^8$ denotes straight-chain or branched alkyl having up to 8 carbon atoms, or benzyl or phenyl, where the latter are optionally substituted up to 3 times by identical or different substituents from the series comprising halogen, hydroxyl, nitro, cyano, trifluoromethyl and trifluoromethoxy or by straight-chain or branched alkyl, alkoxy or alkoxycarbonyl each having up to 6 carbon atoms, carboxyl or by the abovementioned group —NR$^6$R$^7$, in which R$^6$ and R$^7$ have the abovementioned meaning, represents phenyl which is optionally substituted up to 3 times by identical or different substituents from the series comprising halogen, hydroxyl, nitro, trifluoromethyl, trifluoromethoxy, straight-chain or branched alkyl, acyl, and alkoxy or alkoxycarbonyl each having up to 6 carbon atoms or by a group of the formula —NR$^6$R$^7$ or —SO$_2$R$^8$, in which R$^6$, R$^7$ and R$^8$ have the abovementioned meaning, R$^3$ represents hydrogen or straight-chain or branched alkyl having up to 8 carbon atoms, which is optionally substituted by phenyl, or R$^2$ and R$^3$ together represent the radical of the formula =CHR$^{5'}$, in which R$^{5'}$ denotes hydrogen or straight-chain or branched alkyl having up to 8 carbon atoms, which is optionally substituted by halogen, hydroxyl, phenyl or carboxyl or by straight-chain or branched alkoxy or alkoxy carbonyl each having up to 6 carbon atoms, D represents an oxygen or sulphur atom or the

group,

R$^4$ represents hydrogen or straight-chain or branched alkyl having up to 8 carbon atoms, or phenyl, where the latter are optionally substituted up to 3 times by identical or different substituents from the group comprising hydroxyl, halogen, nitro, cyano, carboxyl, trifluoromethyl and trifluoromethoxy, by straight-chain or branched alkoxy, in the case of phenyl also by alkyl, acyl or alkoxycarbonyl each having up to 6 carbon atoms or by a group of the formula —NR$^6$R$^7$ or —SO$_2$R$^8$, in which R$^6$, R$^7$ and R$^8$ have the abovementioned meaning, or for the case in which D represents the

group

R$^4$ represents the group of the formula —SO$_2$R$^8$, in which

R$^8$ has the abovementioned meaning.

4. The method according to claim 3, in which the general formula (I)

A and B are always different and represent a sulphur atom or the group of the formula —CHR$^5$, in which R$^5$ denotes hydrogen or straight-chain or branched alkyl having up to 6 carbon atoms, which is optionally substituted by halogen or hydroxyl, or by straight-chain or branched alkoxy or alkoxy carbonyl each having up to 4 carbon atoms, R$^1$ represents hydrogen or straight-chain or branched alkyl having up to 6 carbon atoms, which is optionally substituted by halogen or hydroxyl, by straight-chain or branched alkoxy, acyl or alkoxy carbonyl each having up to 4 carbon atoms or by a group of the formula —NR$^6$R$^7$, in which R$^6$ and R$^7$ are identical or different and denote hydrogen or straight-chain or branched alkyl having up to 4 carbon atoms, R$^2$ represents hydrogen or represents straight-chain or branched alkyl having up to 6 carbon atoms, which is optionally substituted by hydroxyl or formyl or by straight-chain or branched acyl having up to 4 carbon atoms or by phenyl or benzoyl, each of which is optionally substituted by halogen, nitro or cyano, or by straight-chain or branched alkyl having up to 4 carbon atoms, or represents straight-chain or branched acyl having up to 6 carbon atoms or represents benzoyl which is optionally substituted as described above, or represents a group of the formula $-SO_2R^8$, in which $R^8$ denotes straight-chain or branched alkyl having up to 6 carbon atoms, phenyl or benzyl, where the latter are optionally substituted up to 2 times by identical or different substituents from the series comprising halogen, hydroxyl, nitro, cyano, trifluoromethyl and trifluoromethoxy or by straight-chain or branched alkyl or alkoxy each having up to 4 carbon atoms or by the abovementioned group of the formula $-NR^6R^7$, in which $R^6$ and $R^7$ have the abovementioned meaning, represents phenyl which is optionally substituted up to 2 times by identical or different groups from the series comprising halogen, hydroxyl, nitro, trifluoromethyl, trifluoromethoxy and straight-chain or branched alkyl, acyl, alkoxy or alkoxycarbonyl each having up to 4 carbon atoms or by a group of the formula $-NR^6R^7$ or $-SO_2R^8$, in which $R^6$, $R^7$ and $R^8$ have the abovementioned meaning, $R^3$ represents hydrogen or straight-chain or branched alkyl having up to 6 carbon atoms or benzyl, or $R^2$ and $R^3$ together represent the radical of the formula $=CHR^{5'}$, in which $R^{5'}$ denotes hydrogen or straight-chain or branched alkyl having up to 6 carbon atoms, which is optionally substituted by halogen or hydroxyl, or by straight-chain or branched alkoxy or alkoxy carbonyl each having up to 4 carbon atoms, D represents an oxygen or sulphur atom or the

group, $R^4$ represents hydrogen or straight-chain or branched alkyl having up to 6 carbon atoms or phenyl, where the latter are optionally substituted up to 2 times by identical or different substituents from the series comprising hydroxyl, halogen, nitro, cyano, trifluoromethyl and trifluoromethoxy, by straight-chain or branched alkoxy, acyl or alkoxy carbonyl each having up to 4 carbon atoms or by a group of the formula $-NR^6R^7$ or $-SO_2R^8$, in which $R^6$, $R^7$ and $R^8$ have the abovementioned meaning, or for the case in which D represents the

group, $R^4$ represents the group of the formula $-SO_2R^8$, in which $R^8$ has the abovementioned meaning.

5. The method according to claim 3, in which in the formula (I)

A and B are always different and represent a sulphur atom or the group of the formula $-CHR^5$, in which $R^5$ denotes hydrogen or straight-chain or branched alkyl having up to 4 carbon atoms, $R^1$ represents hydrogen or represents straight-chain or branched alkyl having up to 4 carbon atoms, $R^2$ represents hydrogen or represents straight-chain or branched alkyl having up to 4 carbon atoms, or represents straight-chain or branched acyl having up to 4 carbon atoms, or represents a group of the formula $-SO_2R^8$, in which $R^8$ denotes straight-chain or branched alkyl having up to 4 carbon atoms, phenyl or benzyl, where the latter are optionally substituted by hydroxyl, fluorine, chlorine, bromine, nitro, cyano, methyl, ethyl or methoxy, $R^3$ represents hydrogen or represents straight-chain or branched alkyl having up to 4 carbon atoms, or $R^2$ and $R^3$ together represent the radical of the formula $=CHR^{5'}$, in which $R^{5'}$ denotes hydrogen or straight-chain or branched alkyl having up to 4 carbon atoms, D represents an oxygen or a sulphur atom or the

$R^4$ represents hydrogen or straight-chain or branched alkyl having up to 4 carbon atoms or phenyl, where the latter are optionally substituted by fluorine, chlorine, bromine, nitro, cyano, methoxy or ethoxy or by a group of the formula $-NR^6R^7$ or $-SO_2R^8$, in which $R^6$ and $R^7$ are identical or different and denote hydrogen, methyl or ethyl and $R^8$ has the abovementioned meaning, or in the case in which D represents the

group, $R^4$ represents the group of the formula $-SO_2R^8$, in which $R^8$ has the abovementioned meaning.

* * * * *